United States Patent
Gnansia et al.

(10) Patent No.: US 11,400,291 B2
(45) Date of Patent: Aug. 2, 2022

(54) IMPLANTABLE BATTERY DEVICE FOR STANDARD COCHLEAR IMPLANT

(71) Applicant: Oticon Medical A/S, Smørum (DK)

(72) Inventors: Dan Gnansia, Vallauris (FR); Nicolas Veau, Burbank California, CA (US); Yannick Vaiarello, Vallauris (FR)

(73) Assignee: Oticon Medical A/S, Smørum (DK)

( * ) Notice: Subject to any disclaimer, the term of this patent is extended or adjusted under 35 U.S.C. 154(b) by 145 days.

(21) Appl. No.: 16/557,744

(22) Filed: Aug. 30, 2019

(65) Prior Publication Data
US 2020/0069944 A1    Mar. 5, 2020

(30) Foreign Application Priority Data

Aug. 31, 2018  (EP) .................................. 18191951

(51) Int. Cl.
*A61N 1/36*  (2006.01)
*A61N 1/05*  (2006.01)
(Continued)

(52) U.S. Cl.
CPC ....... *A61N 1/36038* (2017.08); *A61N 1/0541* (2013.01); *A61N 1/3787* (2013.01);
(Continued)

(58) Field of Classification Search
CPC .............. A61N 1/36038; A61N 1/0541; A61N 1/3787; A61N 1/37229; H04R 25/554; H04R 2225/55
(Continued)

(56) References Cited

U.S. PATENT DOCUMENTS

2006/0183965 A1* 8/2006 Kasic, II ............. H04R 25/606
                                                    600/25
2011/0257703 A1  10/2011 Kerber et al.
2018/0050197 A1*  2/2018 Mazanec ........... A61N 1/37223

FOREIGN PATENT DOCUMENTS

CN    101980412 A    2/2011
CN    106787134 A    5/2017
(Continued)

OTHER PUBLICATIONS

Extended European Search Report issued in European Patent Application No. 18191951.5 dated Feb. 14, 2019.

*Primary Examiner* — Mallika D Fairchild
*Assistant Examiner* — Minh Duc G Pham
(74) *Attorney, Agent, or Firm* — Birch, Stewart, Kolasch & Birch, LLP

(57) ABSTRACT

An implantable battery device is disclosed, which comprises a battery, a first antenna, a second antenna, and a driving unit. The first antenna is configured to inductively supply energy from the battery to a first device and to transmit information received from a processing unit to the first device. The second antenna is provided for wireless communication with a second device. The driving unit is configured to operate the first antenna according to control signals received from the processing unit. The processing unit is configured to transmit control signals to the driving unit to control the inductive supply of energy to the first device, to receive information via the second antenna from the second device, and to transmit information received via the second antenna from the second device to the first device via the first antenna driven by the driving unit.

18 Claims, 9 Drawing Sheets

(51) Int. Cl.
*A61N 1/378* (2006.01)
*A61N 1/372* (2006.01)
*H04R 25/00* (2006.01)

(52) U.S. Cl.
CPC ........ *A61N 1/37229* (2013.01); *H04R 25/554* (2013.01); *H04R 2225/55* (2013.01)

(58) Field of Classification Search
USPC .......................................................... 607/57
See application file for complete search history.

(56) References Cited

FOREIGN PATENT DOCUMENTS

EP         0 999 874 A1    5/2000
WO     WO 99/06108 A1    2/1999

* cited by examiner

IMPLANTABLE BATTERY DEVICE FOR STANDARD COCHLEAR IMPLANT

FIELD

The present disclosure relates to an implantable battery device. More particularly, the disclosure relates to implantable battery device for use with a standard cochlear implant that can be used as a wireless relay device for audio signals.

BACKGROUND

Cochlear implants for assisting users having hearing disabilities are known. Current cochlear implant systems are composed by an external device (called BTE device, "Behind The Ear" device or sound processor) and an implantable device (called "cochlear implant"). Typically, a cochlear implant is implanted into the head of the user and comprises a receiver coil and an electrode. The electrode is implanted close to the cochlea and provides stimuli to the cochlea of the user, while the receiver coil is implanted at a position in the head of the user at the rear side of the head, where it can be wirelessly connected to an external transmitter coil.

The transmitter coil generates an alternating electromagnetic field, which inductively transmits information and energy to the receiver coil of the cochlear implant. The transmitter coil is connected to the Behind-the-ear hearing aid device, which provides e.g. a microphone, a battery, and a sound processor for processing audio signals recorded by the microphone, for processing the audio signals according to predetermined processing and settings, and providing the processed audio signals (information) and energy from the battery to the cochlear implant using the link between the transmitter coil and the receiver coil.

However, since there is biological tissue between the receiver coil and the transmitter coil, the transmission of energy to the receiver coil can heat up the biological tissue between the coils and in the vicinity of the coils, thus causing a damage to the tissue and/or causing an uncomfortable feeling to the user. Therefore, in order to lower the magnetic field strength, the coils are made to be relatively large, thus causing an aesthetic issue for the user. Even though the coils are arranged e.g. to be covered by hair and are typically arranged on the backside of the head of the user, there is still an uncomfortable feeling to the user of the hearing aid due to the large transmitter coil being placed visibly on the backside of the head of the user.

It is known that a part of the deafness community does not want to wear a cochlear implant because of the large size of the external device (processor and antenna on the skull).

Therefore, there is a need to provide a solution that addresses at least some of the above-mentioned problems. The present disclosure provides at least an alternative to the prior art.

SUMMARY

According to an aspect of the application, an implantable battery device is provided, which comprises a battery, a first antenna, a second antenna, and a driving unit. The first antenna is configured to supply energy inductively from the battery to a first device and to transmit information received from a processing unit to the first device. The second antenna is provided for wireless communication with a second device. The driving unit is configured to operate the first antenna according to control signals received from the processing unit. The processing unit is configured to transmit control signals to the driving unit to control the inductive supply of energy to the first device, to receive information via the second antenna from the second device, and to transmit information received via the second antenna from the second device to the first device via the first antenna driven by the driving unit.

The implantable battery device of the present invention allows for transmitting information from the second device to the implantable battery device, thus removing the need of using large coils for the transmission of energy from the second device. Since the energy for operating the first device is taken from the implantable battery device, the energy does not have to be transmitted from the second device. Hence, the second device can be made smaller, while also the second antenna can be made smaller than the first antenna, since only data needs to be transmitted. Hence, the aesthetic appearance can be made more attractive to users.

Further, the driving unit may be configured to control an amplitude of an electromagnetic field emitted from the first antenna according to control signals received from the processing unit.

This allows for the processing unit to control the amount of energy that is being transmitted to the first device. Hence, the battery lifetime can be prolonged.

Furthermore, the driving unit may be configured to modulate the amplitude and/or a frequency of the electromagnetic field emitted from the first antenna according to the information received from the processing unit.

This allows for controlling the second antenna for transmission of energy and information to the first device. Furthermore, the information can be efficiently transferred, while also the transmission of energy can be improved.

In addition, the processing unit may be configured to transmit information to the second device via the second antenna.

This allows for sending back information to the second device. Such information may include for example information on the status of the first device. When the information is further transmitted to a device having a user interface such as a SmartPhone, the user can in this way take notice of certain parameters of the first device or the implantable battery device.

Further, the processing unit may be configured to obtain a charge state of the battery, and to control the inductive supply of energy to the first device depending on the charge state.

This allows stopping the energy transfer process in case a certain lower threshold of the battery charge state is underrun, for example. Further, this allows reducing the amount of transferred energy depending on certain parameters.

Furthermore, the first antenna may comprise a magnetically interacting part in a center of the first antenna for alignment of the first antenna with at least one other antenna.

Some implanted devices comprise an antenna having a magnet for aligning an external device to the antenna of the implanted device. Hence, a magnetically interacting part may improve the efficiency of the coupling, while it further allows to waive extra fixing means. Alternatively, a magnet may be provided on the first antenna, hence allowing to improve a coupling efficiency to an external device.

In addition, the processing unit may be configured to control the inductive supply of energy to the first device depending on information received by the second device.

This allows to control the transmission of energy to the first device depending on a user interaction, for example.

Further, the battery may be a rechargeable battery, and the implantable battery device may further comprise a battery charging unit, which is configured to receive energy via the first antenna from another device for recharging the battery.

This allows for extending the lifetime of the implantable battery device. Hence, less surgery is required for a user for changing the implant or the battery, hence improving a comfort for the user.

Furthermore, the first device may be a cochlear implant, and the second device may be a hearing aid sound processor.

Even further, the processing unit may be configured to process information from the hearing aid sound processor to be transmitted to the cochlear implant.

This allows for applying the above-described benefits to hearing devices, especially cochlear implants. Using the described implantable battery device, existing cochlear implants can be retrofitted so that the aesthetic appearance can be improved for existing users of cochlear implants.

According to another aspect of the application, a hearing aid sound processor is provided, which is configured to transmit audio signals to an implantable battery device according to any one of the above aspects using a wireless link.

This allows for providing a dedicated sound processor, which can be smaller in size due to a reduction in battery capacity, hence being more attractive for users to wear.

According to yet another aspect of the application, a charging device is provided, which is configured to charge an implantable battery device according to any one of the above aspects.

This allows for providing of a dedicated charger device, which does not need to be a sound processor. Indeed, a separate charger device may be provided, which is attached or connected to the implantable battery device only if recharging is required. This further allows to reduce the size of the external sound processor, as the charging functionality does not have to be provided in the sound processor.

The implantable battery device may comprise only a single antenna configured to transmit and receive energy and data between the first device and the second device. Thereby, you avoid having two antennas.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
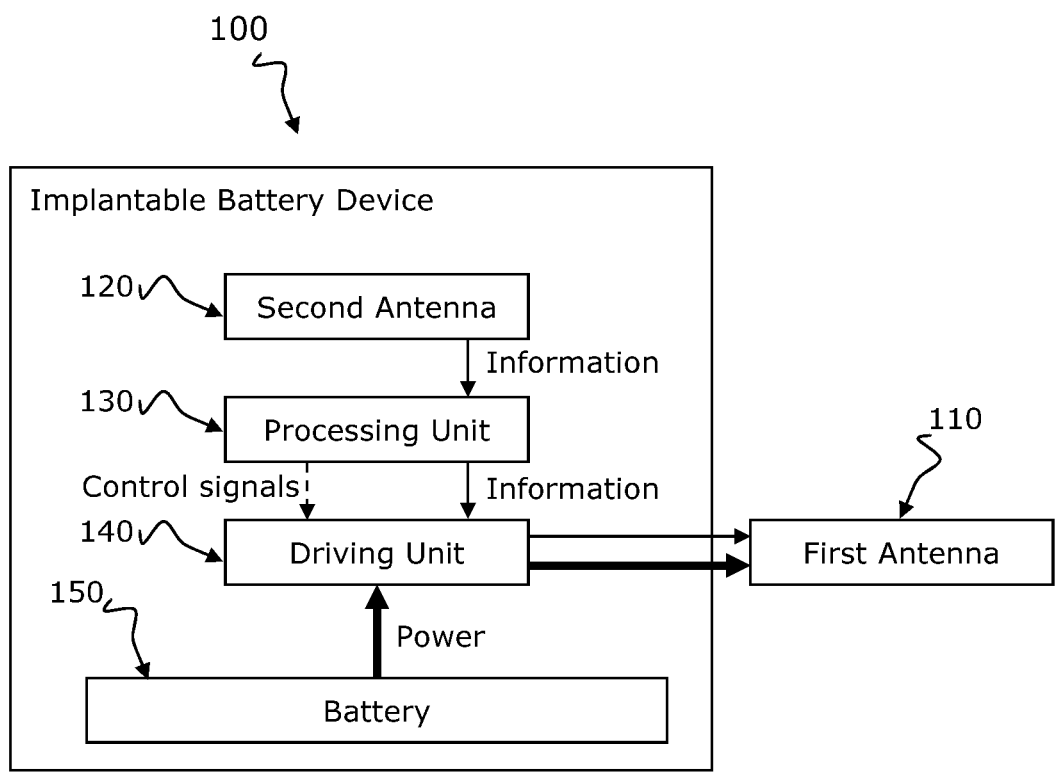
FIG. 1 illustrates an implantable battery device according to an embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant. A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefiting from the functioning of the hearing devices. A wired or wireless communication link between the at least one hearing device and the auxiliary device is established that allows for exchanging information (e.g. control and status signals, possibly audio signals) between the at least one hearing device and the auxiliary device.

Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

Figure 6A:
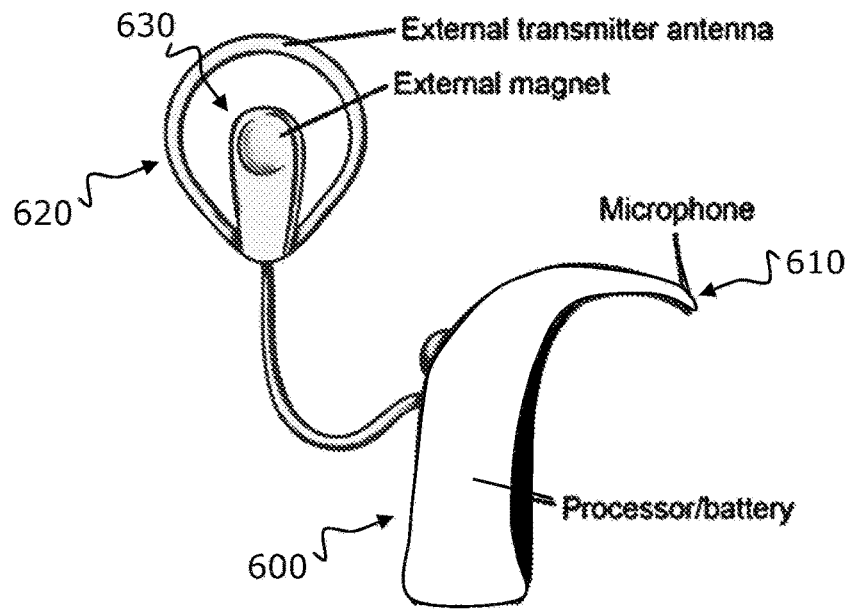
FIG. 6A illustrates a sound processor for a cochlear implant of the prior art.
Figure 6B:
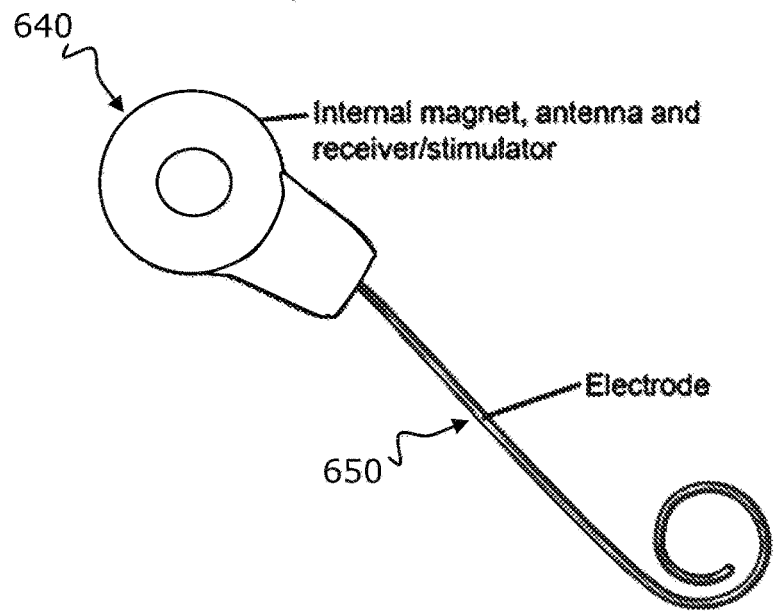
FIG. 6B illustrates a cochlear implant of the prior art.

Patients suffering from deafness or severe to profound hearing loss caused by severe loss of inner ear hair cells are often candidates for a cochlear implant solution as depicted in FIGS. 6A and 6B. Current solutions consist of an implanted part 640, 650 (the cochlear implant) consisting of an antenna 650 and electronics 640 placed under the skin.

A cochlear implant typically includes i) an external part 600 (so called "Behind the ear" device (BTE device) or sound processor) for picking up by a microphone 610 and processing sound from the environment, and for determining sequences of pulses for stimulation of the electrodes 650 in dependence on the current input sound, ii) a (typically wireless, e.g. inductive) communication link for simultaneously transmitting information about the stimulation sequences and for transferring energy to iii) an implanted part 640, 650 (so called implant) allowing the stimulation to be generated and applied to a number of electrodes 650, which are implantable in different locations of the cochlea allowing a stimulation of different frequencies of the audible range. That is, the cochlear implant has e.g. an electrode array 650 that is placed in the cochlear with the purpose of stimulating the hearing nerves directly electrically. Such systems are e.g. described in U.S. Pat. No. 4,207,441 and in U.S. Pat. No. 4,532,930.

In an aspect, the hearing device comprises a multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes 650 may be inserted in cochlea of a recipient. Preferably, the individual electrodes are spatially distributed along the length of the carrier to provide a corresponding spatial distribution along the cochlear nerve in cochlea when the carrier is inserted in the cochlea.

As mentioned above, the external part 600, 620, 630 and the cochlear implant 640 are both linked by an inductive field in order to deliver, from the sound processor to the implant, the energy for the cochlear implant and the information for the stimulation. The inductive field is typically generated by an excitation coil 620 (in the following: transmitter coil) and is picked up by a receiver coil 640 connected to the implant. That is, current systems work with an inductive field generated by the external antenna, which is configured to deliver the power and data to the implant.

That is, the outer part consists of a transmitter antenna 620 placed over the implanted antenna 640, which is connected to the sound processor 600 placed behind the ear or integrated with the outer antenna. The external part holds one or more relatively large batteries to supply the sound processor and the cochlear implant 640, 650 through inductive coupling through the skin.

This kind of architecture has an aesthetic issue for the user as the inductive link is transmitted by a large visible antenna 620 placed on the patient's skull (e.g. on the rear side of the user's head). Hence wearing a cochlear implant may cause an uncomfortable feeling to the user, because of the large size of the external device (sound processor 600 with antenna part 620 on the skull). In other words, external components are often very visible due to the size of the antenna 620 and the large batteries. This is cosmetically not attractive for the users.

The present invention however, provides a new system architecture in order to reduce the size of the external device 600, 620 and to increase its aesthetic appearance. Further, the invention is related to a new system architecture in order to reduce the external device size and increase the aesthetic benefit.

In certain embodiments of the invention as depicted in FIGS. 5A to 5G, a battery 510 may be included in the implanted device 500. This allows for transmitting only data from the external sound processor to the implant, since the energy for the cochlear implant is taken from the battery 510 in the implant 500. Hence, the external antenna can be made smaller, which increases the aesthetic appearance of the cochlear implant as a whole.

With a battery 510 included in the implant, only the data must be delivered to the cochlear implant 500, which reduces the requirements for the communication protocol.

Figure 5A:
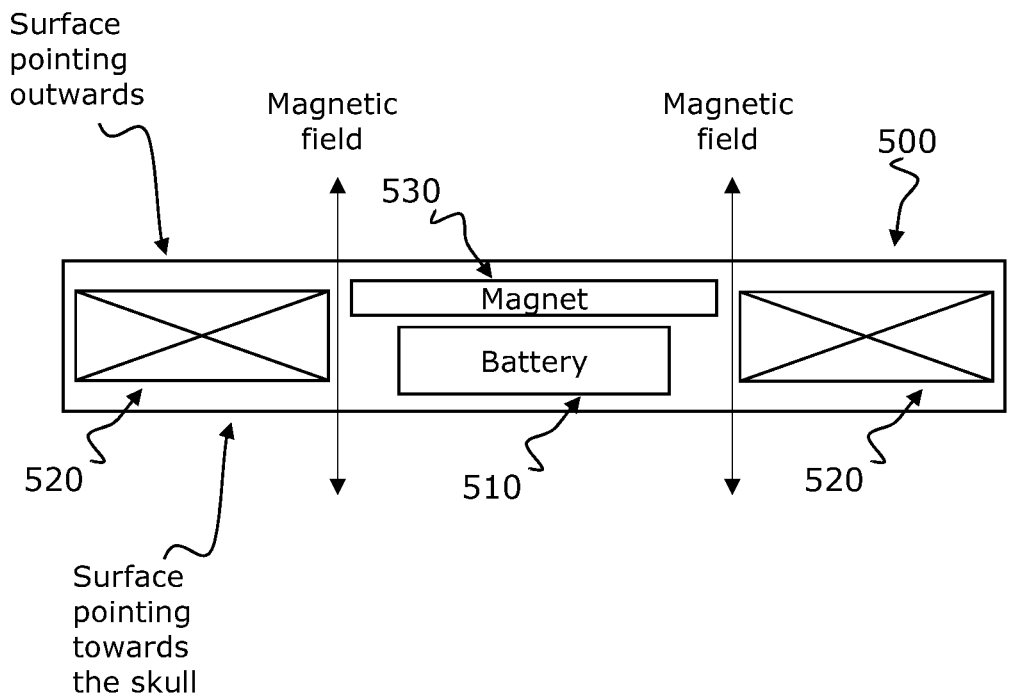
FIG. 5A shows a cross-section through an implantable cochlear implant according to an embodiment of the disclosure.

However, in the embodiments depicted in FIGS. 5A to 5G, different embodiments having a battery 510 in the cochlear implant 500 are shown. Note that the embodiments of a generally circular shape are shown. However, the invention is not limited to being circular. FIG. 5A shows a cross-section through an implantable cochlear implant 500 according to an embodiment of the disclosure. The cochlear implant 500 comprises a coil 520, in the middle of which a battery 510 and a magnet 530 are placed, for example. The radius or dimension of the magnet 530 shall be equal or larger than the battery 510 in order to shield the battery 510 from the electromagnetic field imposed on the cochlear implant 500 by an external device (not shown). Furthermore, the magnet 530 may be arranged on a side of the battery 510 pointing outwards, while the battery 510 is placed on a side of the magnet 530 towards the skull. Hence, the magnet 530 is acting as a shield to protect the battery 510 from the electromagnetic field indicated by the arrows. The magnetic field may be an alternating magnetic field. Hence, the battery 510 can be shielded from the electromagnetic field which otherwise will induce heat to the battery 510 due to eddy current heating. Therefore, a lifetime of the battery 510 can be extended as compared to the unshielded case.

Figure 5B:
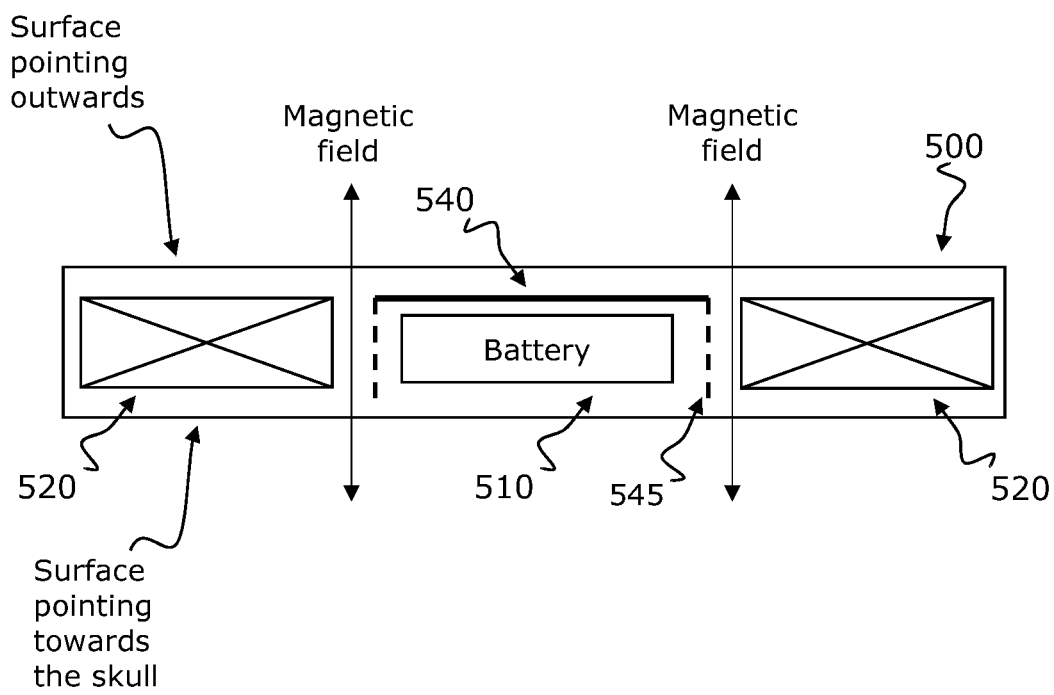
FIG. 5B shows a cross-section through another example of an implantable cochlear implant according to an embodiment of the disclosure.

FIG. 5B shows a modification of the embodiment above with the difference that a shield 540 is configured to shield the battery 510 from unwanted electromagnetic induction from an external charger device, and additional shielding elements 545 improve the shielding effect. Such shield 540 may be placed on the outwards pointing side of the battery 510. Hence, the battery 510 can be shielded from the electromagnetic field which otherwise will induce heat to the battery. Therefore, a lifetime of the battery 510 can be extended.

Figure 5C:
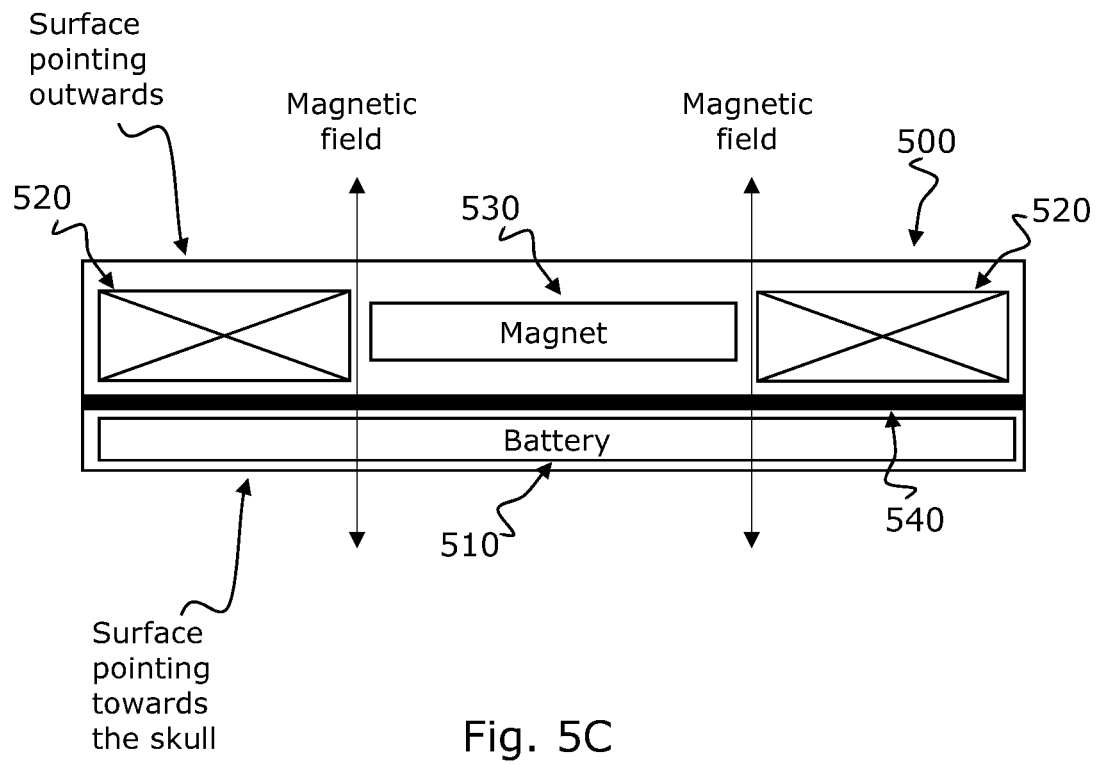
FIG. 5C shows a cross-section through yet another example of an implantable cochlear implant according to an embodiment of the disclosure.

FIG. 5C shows a further modification of the embodiment above with the difference that a shield 540 is configured to shield the battery 510 from unwanted electromagnetic induction from an external charger device. However, as opposed to the embodiments above, when the battery 510 is placed below the coil 520 and the magnet 530, the battery 510 can be made much larger. The shield 540 can again be placed on the outwards pointing side of the battery 510. Hence, the battery 510 can be shielded from the electromagnetic field which otherwise will induce heat to the battery 510. Therefore, a lifetime of the battery 510 can be extended.

Figure 5D:
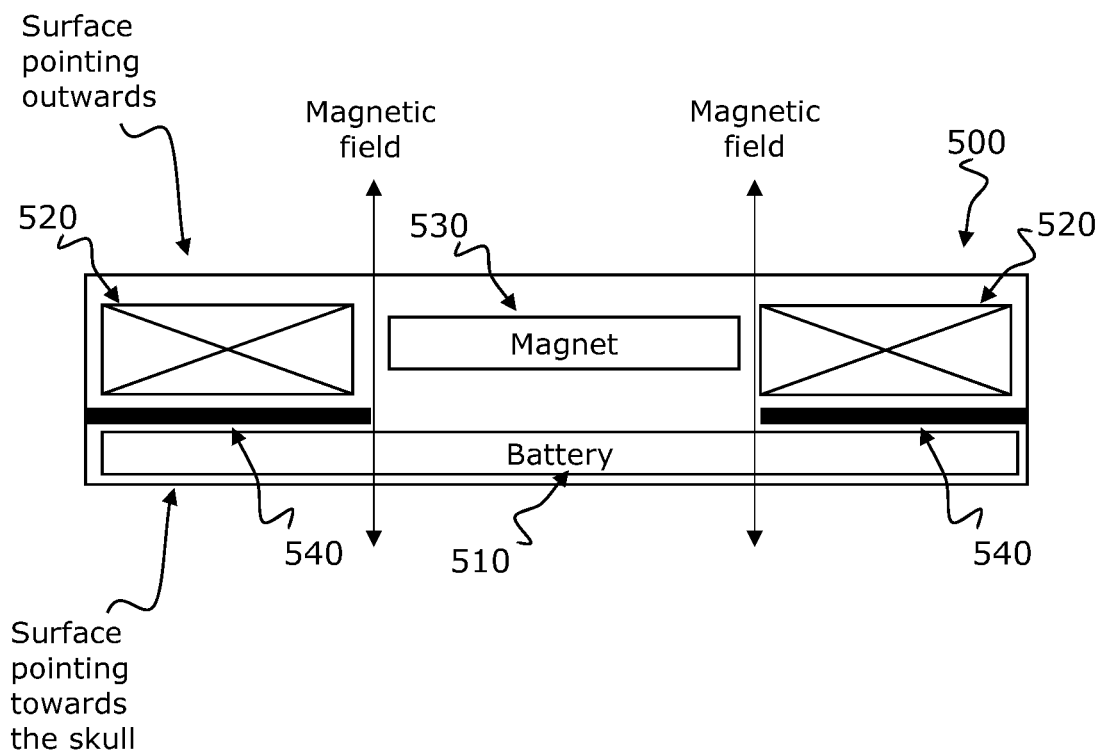
FIG. 5D shows a cross-section through yet another example of an implantable cochlear implant according to an embodiment of the disclosure.

FIG. 5D shows a further modification of the embodiment above with the difference that a shield 540 is configured to shield the battery 510 from unwanted electromagnetic induction from an external charger device. However, as opposed to the embodiments above, the shield 540 may not extend across the full length of the battery 510, but may have e.g. a hole in the middle. The shield 540 can again be placed on the outwards pointing side of the battery 510. Hence, the battery 510 can be shielded from the electromagnetic field which otherwise will induce heat to the battery 510. Therefore, a lifetime of the battery 510 can be extended.

Figure 5E:
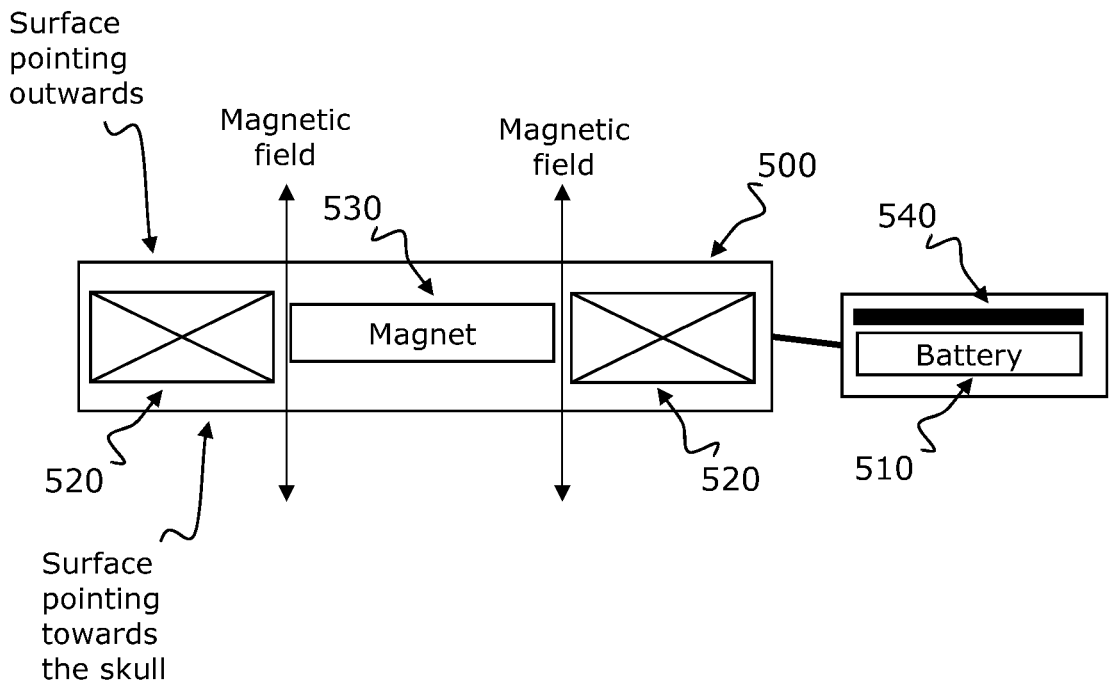
FIG. 5E shows a cross-section through yet another example of an implantable cochlear implant according to an embodiment of the disclosure.

FIG. 5E shows a further modification of the embodiment above with the difference that the battery 510 and a shield 540 are provided in an extra compartment, which is connected by wires to the main housing of the cochlear implant 500. The radius or dimension of the shield 540 shall be equal or larger than the battery 510 in order to shield the battery 510 from the electromagnetic field. Since the magnetic field will be lower at the remote location of the extra compartment, it is again possible to shield the battery 510 from unwanted electromagnetic induction from an external charger device. The shield 540 may again be placed on the outwards pointing side of the battery 510. Hence, the battery 510 can be shielded from the electromagnetic field which otherwise will induce heat to the battery 510. Therefore, a lifetime of the battery 510 can be extended.

Figure 5F:
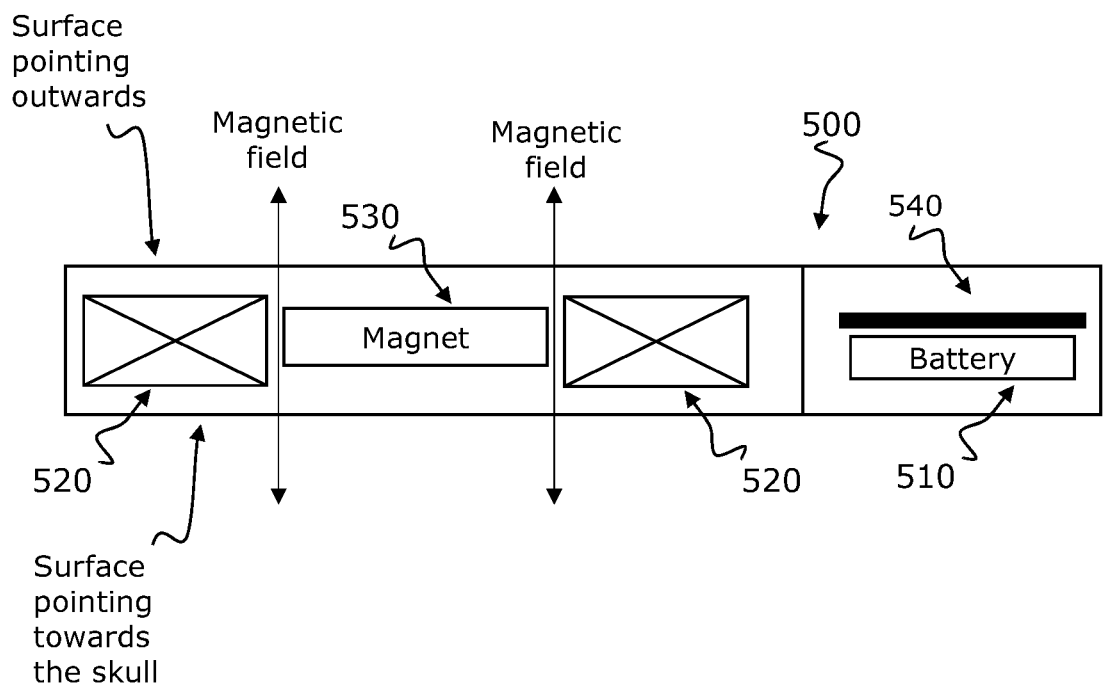
FIG. 5F shows a cross-section through yet another example of an implantable cochlear implant according to an embodiment of the disclosure.

FIG. 5F shows a further modification of the embodiment above with the difference that the battery 510 and a shield 540 are provided in an extra compartment, which is directly connected to the main housing of the cochlear implant 500. The radius or dimension of the shield 540 shall be equal or larger than the battery 510 in order to shield the battery 510 from the electromagnetic field. Since the magnetic field will be lower at the location of the extra compartment, it is again possible to shield the battery 510 from unwanted electromagnetic induction from an external charger device. The shield 540 may again be placed on the outwards pointing side of the battery 510. Hence, the battery 510 can be shielded from the electromagnetic field which otherwise will induce heat to the battery 510. Therefore, a lifetime of the battery 510 can be extended.

Figure 5G:
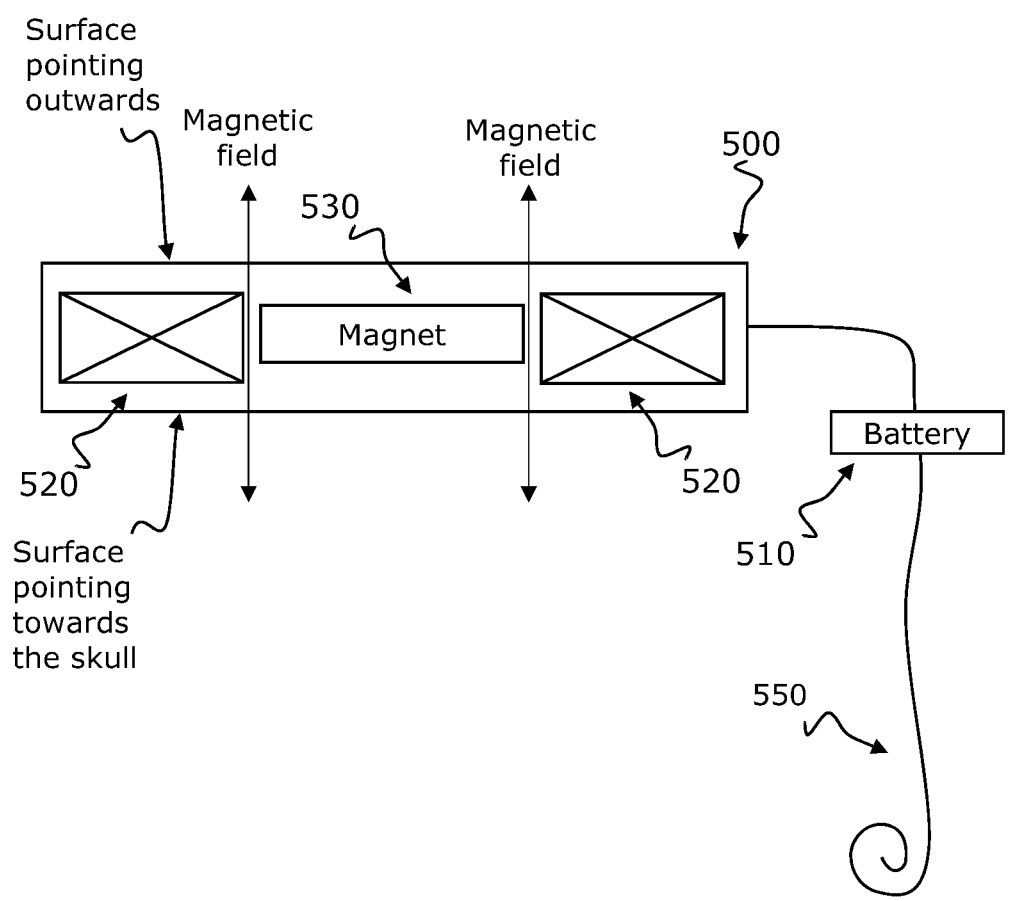
FIG. 5G shows a cross-section through yet another example of an implantable cochlear implant according to an embodiment of the disclosure.

FIG. 5G shows a further modification of the embodiment above with the difference that the battery 510 is provided in an extra compartment, which is arranged on the electrode wire 550 to the cochlea. Since the magnetic field will be lower at the location of the extra compartment, it is again possible to shield the battery 510 from unwanted electromagnetic induction from an external charger device. Hence, the battery 510 can be shielded from the electromagnetic field which otherwise will induce heat to the battery 510. Therefore, a lifetime of the battery 510 can be extended.

In certain embodiments of the invention, a temperature sensor may additionally be placed on or at the battery. In such a case, the cochlear implant 500 may be configured to transmit the temperature of the battery 510 to the external charger via the same coil 520, which is being used for charging the battery 510. Hence, the external charger can be configured to control the charging process according to the temperature of the battery, so that heating of the battery can be avoid or reduced. Hence, the temperature can be modulated such that the same coil can be used for both charging and communication at the same time.

In certain embodiments of the invention, the link between the external device and the cochlear implant can be achieved using other radiofrequency protocols, which may transmit data only.

This allows using other frequencies in a more flexible way, because the efficiency on the radiofrequency in term of transmission of energy can be neglected for the normal use case. That is, the external device can have a lower footprint and the antenna can be made smaller and a larger distance can be achieved from the external antenna to the antenna of the implant. The use of a wireless communication technology between the sound processor and cochlear implant can use a technology that does not take up much space, such as a near-link coil, a Bluetooth antenna, or the like.

The use of a low power radio system (such as near field magnetic) with a range sufficient to reach the contralateral ear allows a single sound processor to be placed in one ear to optionally drive two implants (ipsi- and contralateral).

In certain embodiments of the invention, alternating inductive fields are used for transmitting energy and/or information. When using alternating inductive fields, standard electronic components can be used, hence saving costs.

In certain embodiments of the invention, the BTE device may be included inside an antenna, since no inductive antenna on the skull is necessary during normal operation. In this case, the size of the antenna can be greatly reduced, since smaller batteries can be used since no energy of the BTE device is used to supply energy to the implant.

In certain embodiments of the invention, the antenna may be included inside a BTE device, since no inductive antenna on the skull is necessary during normal operation. In this case, the battery of the external sound processor can be greatly reduced, such as e.g. more than 70% of the battery size used today, which are used to supply energy to the implant. Hence, the sound processor can look like a normal hearing aid, which leads to a great benefit for the user. That is, the sound processor part can be reduced in size by using a minimal battery size and using a form factor that is small enough to be completely or almost completely hidden, e.g. in the ear canal (e.g. IIC style).

Having the sound processor for the cochlear implant hidden in the ear canal provides for the benefit, that the sound processor becomes almost invisible. Furthermore, the sound processor is not in the way, when e.g. combing the hair or wearing glasses. Even more, in case the sound processor is placed in the ear canal, the sound processor is more or less protected from direct weather exposure such as rain, snow, sunlight, wind, etc., and external influences, such as high or low temperature, high or low humidity, while it is also less exposed to turbulent wind noise. Furthermore, the natural outer ear sound shaping (directionality) is preserved when having the receiving microphone sitting inside the ear canal opening. In addition, the sound processor is fully accessible by the user and hence, allows service, upgrades and replacements without requiring any surgery or any hardware modification of the implant. Additionally, the cochlear implant does not require a magnet for holding the external antenna, and can thus be made smaller, slimmer and lighter. Further, the cochlear implant can be placed more freely as in the case of a closely matching external antenna, which needs to transmit energy to the cochlear implant, since fewer restrictions are imposed on the cochlear implant.

In certain embodiments of the invention, the cochlear implant may comprise a rechargeable battery. Since the use of a normal battery will lead to a rather short lifetime, and hence to an early replacement of the cochlear implant, a rechargeable battery allows for a longer lifetime of the cochlear implant.

Hence, in certain embodiments of the invention, the user may be required to recharge the implantable battery device 100 using for example an external device, which may be a sound processor having an inductive link inside and enough batteries to charge the rechargeable battery of the implant. Thus, the user may install the connection to an inductive antenna only when it is necessary to recharge the rechargeable battery of the implant, using e.g. a connector on the sound processor, to which the inductive transmitter coil can be connected. From an aesthetic point of view, the user has the benefit to wear the sound processor behind the ear without the large inductive antenna most of the time, since the processor does not need to have an inductive link inside in order to improve the device's aesthetic. Hence, in the normal use case, the large inductive antenna is not visible, thus providing the advantages of the invention. Once, the user wants to recharge the rechargeable battery, the user can connect the large inductive antenna to a respective connector of the sound processor, and position the large inductive antenna on the rear side of his head over the implanted antenna, and start the recharging process using the batteries in the sound processor as an energy source.

In certain embodiments of the invention, the external part may optionally also have a receiver (speaker) implemented for invisible combined acoustic and electric stimulation, which effectively makes it a hearing instrument with modified firmware to control also the cochlear implant via the wireless technology.

Further, in certain embodiments of the invention, the user may also use an external device for charging, which is different from the sound processor, that is, another device may be used to charge the battery. For example, the user may use a dedicated charger device, which may be a connected to the user's skull for example for night-time charging during sleep of the user. Such a separate inductive charging system for the cochlear implant can be provided e.g. under a pillow in the user's bed for night charging.

In certain embodiments, such a dedicated charger device may be battery driven or may be connected to mains power. It can further be mechanically designed such, that the sound processor is included in the antenna and may be used only to charge the battery (very few times in the day or in the night). This also provides a great aesthetic benefit to the user, since the user does not have to wear the large sound processor device all the time.

Figure 4:
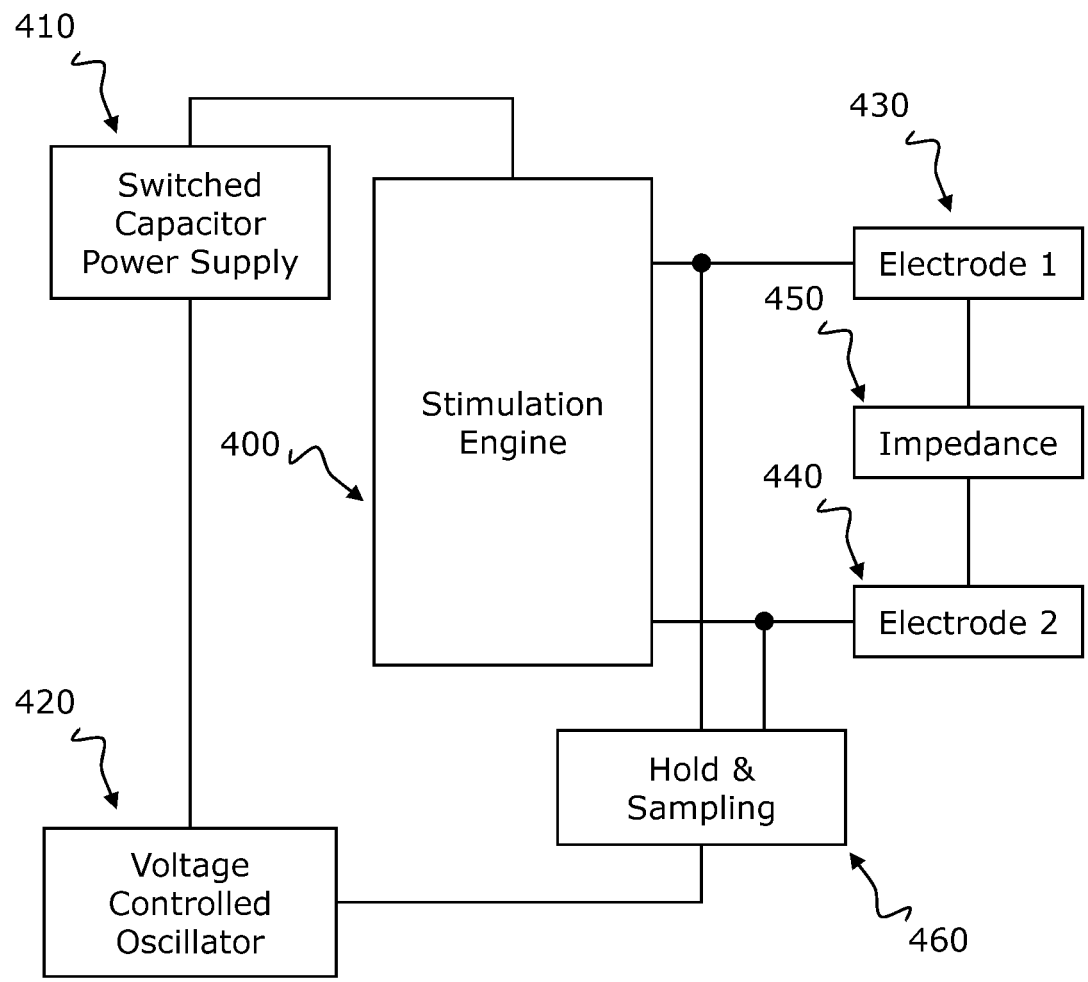
FIG. 4 illustrates a schematic communication diagram according to an embodiment of the disclosure.

In order to improve battery lifetime of the cochlear implant, in certain embodiments of the invention, techniques may be applied for reducing the energy consumption of the implant. With reference to FIG. 4, such a technique is explained. The cochlear implant needs a minimum voltage in order to supply the device correctly with energy and to allow a minimum of voltage compliance. The voltage compliance is the minimum voltage necessary to deliver the desired stimulation current into the patient impedance 450, i.e. the power supply voltage of the device, which corresponds to the possible maximum impedance at the maximum current available.

In order to improve battery lifetime, in certain embodiments of the invention, an energy source may be implanted, that is, the cochlear implant may receive energy from another implanted device.

The cochlear implant needs a minimum of voltage in order to supply power to the device correctly and to allow a minimum of voltage compliance.

The voltage compliance is the minimum voltage necessary to deliver the desired stimulation pulses to the implanted electrodes 430, 440. These electrodes 430, 440 through being connected to the cochlear of the user represent a certain electrical impedance 450. That is, the required power supply voltage of the device corresponds to the maximum impedance of the electrode array multiplied with the maximum current that is required for suitable stimulation.

Since the power supply is usually implemented with a regulator device, depending of the patient having a cochlear implant having certain maximum current and electrode impedance, a part of the energy is directly converted in electrical loss, that is, in heating into the device.

As an example, the implant may be powered at 5V, while the parameters of the cochlear implant of a user are an impedance of 2 kΩ and a required stimulation current of 1 mA. Hence, the minimum power supply to guarantee the stimulation is 2 kΩ×1 mA=2V, which is lower than the 5V that are supplied to the cochlear implant. That is, in this example the external device sends more energy than is required (here, 3V) and therefore, the energy storage of the BTE device is used faster.

In order to improve the battery lifetime without any compromise with the voltage compliance, this user would like to address a loop control architecture from the patient impedance to the implant power supply according to FIG. 4.

This loop is based on a voltage measurement done during the standard stimulation behavior between electrodes 430, 440. The patient's impedance 450 is calculated during the stimulation based on a sample and hold circuitry 460 which determines a voltage corresponding to the electrode impedance 450. This voltage is used for example in a voltage controlled oscillator circuitry 420 in order to tune the sampling frequency of a regulator in the Stimulation Engine 400 based on a switch capacitor 410. Thus, the power supply of the implant, output of the regulator, is tuned as close as possible to the minimum voltage necessary for the user's voltage compliance.

This loop can be activated for example for each stimulation or between a specific time, depending of the impedance change or the calculation load of the implant.

In certain embodiments of the invention, a battery 150 may be provided in a implanted battery device 100 as depicted in FIG. 1. An implanted battery device 100 needs to be serviceable, replaceable, or removable during e.g. MRI examination, independently from the rest of the cochlear implant. Also, in case of a battery failure, the cochlear implant needs to remain functional. Hence, an implantable battery device 100 having a battery 150 may be required not to have a physical connector to the cochlear implant, which is challenging in implantable context. That is, not having a physical connector to an implanted cochlear implant is an additional benefit due to improved failure safety. Hence, using the present embodiment of the invention, any standard cochlear implant may be transformed into a more implantable solution without the need to remove the implant, which can be particularly useful for pediatric implantation where implanting a cochlear device having a battery may be too big for a young user of an cochlear implant, but where the user could benefit from an implantable battery device later.

Hence, FIG. 1 shows an implantable battery device 100 according to an embodiment of the invention, which is introduced as a third part to a cochlear implant system, additional to a cochlear implant (not shown in FIG. 1) and a sound processor (not shown in FIG. 1). The implantable battery device 100 comprises a first antenna 110 providing an inductive link to a first device 310, and a second antenna 120 providing a wireless link to a second device 320. The first antenna 110 is provided to couple to the inductive antenna of the first device 310, and can transmit data and energy to the first device 310. The implantable battery device 100 further features a processing unit 130, and a driving unit 140.

The implantable battery device 100 is surgically placed next to the first device 310, with the first antenna 110 inductively coupled to the receiving antenna of the first device. The inductive antenna 110 may be made from a thin and soft material (e.g., electrical wires in silicone). The battery 150 may be e.g. a rechargeable battery or a super capacitor.

Figure 3A:
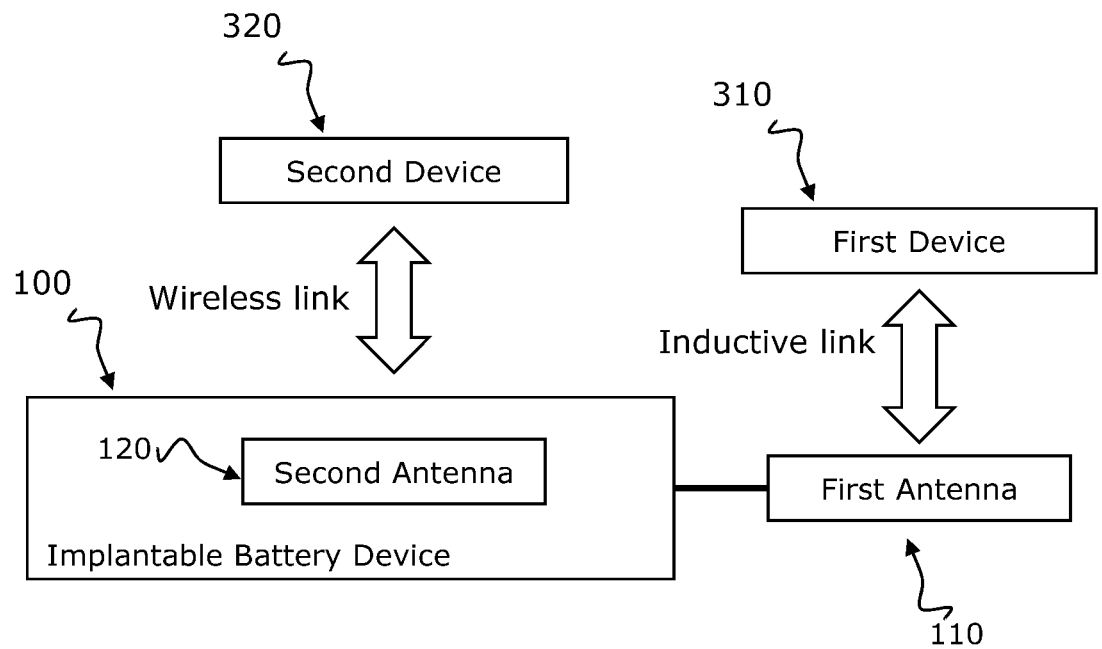
FIG. 3A illustrates a schematic communication diagram according to an embodiment of the disclosure.

FIG. 3A illustrates a schematic communication diagram according to an embodiment of the disclosure. In FIG. 3A, the normal use case is depicted. An external second device, that is, e.g. a BTE device of a cochlear implant system may provide a microphone as well as wireless capabilities (wireless link), while it does not need to have an inductive antenna for transmitting energy. The microphone can capture sound and transmit all relevant data (information) to the implantable battery device 100 via the wireless link via the second antenna 120. With reference to FIG. 1, the processing unit 130 receives the information via the second antenna 120, and processes the information to be suitable for stimulating the electrodes of the cochlear implant. The processing unit 130 sends the processed information to the driving unit 140 together with control signals, such as e.g. the amplitude of the electromagnetic field that is to be generated. The driving unit 140 then drives the first antenna 110 to generate an inductive field for the transmission of energy and information to the first device 310 via the inductive link.

In other words, the implantable battery device 100 therefore acts as a relay between the external microphone of the sound processor 320 and the cochlear implant 310: audio information will be received by the cochlear implant 310 from the microphone in the external part 320 through the wireless link to the implantable battery device 100, while energy and audio information will be delivered from the implantable battery device 100 to the cochlear implant 310 through the implanted inductive first antenna 110.

That is, an implantable battery device 100 is provided which comprises a battery 150, a first antenna 110, configured to inductively supply energy from the battery 150 to a first device 310 (the cochlear implant), and to transmit information received from a processing unit 130 to the first device 310. The implantable battery device 100 further comprises a second antenna 120 for wireless communication with a second device 320 (the BTE device), and a driving unit 140, configured to operate the first antenna 110 according to control signals received from the processing unit 130, wherein the processing unit 130 is configured to transmit control signals to the driving unit 140 to control the inductive supply of energy to the first device 310, receive information via the second antenna 120 from the second device 320, and to transmit information received via the second antenna 120 from the second device 320 to the first device 310 via the first antenna 110 driven by the driving unit 140.

The driving unit 130 may further be configured to control an amplitude of an electromagnetic field emitted from the first antenna 110 according to control signals received from the processing unit 140. For example, the transmission of energy may be stopped or started depending on the charge state of the battery 150, or on instructions received from the second device 320, e.g. in order to temporarily switch off the cochlear implant.

The driving unit 130 may further be configured to modulate the amplitude and/or a frequency of the electromagnetic field emitted from the first antenna 110 according to the information received from the processing unit 140. The modulation may be matched e.g. to improve an efficiency of an energy transfer or may depend on parameters of the cochlear implant of the user, such as the impedance of the electrode array.

This solution allows to transform any cochlear implant into a more implantable system, without any implanted connector. The implantable battery device 100 can be removed or replaced with the cochlear implant in place and unaltered, or placed later after the first cochlear implant surgery. In case of a battery failure or battery replacement (following battery failure or MRI examination), this solution avoids all risks for the cochlear implant.

Furthermore, the battery of the external sound processor can be greatly reduced, such as e.g. more than 70% of the battery size used today, which are used to supply energy to the implant. Hence, the sound processor can look like a normal hearing aid, which leads to a great benefit for the user. That is, the sound processor part can be reduced in size by using a minimal battery size and using a form factor that is small enough to be completely or almost completely hidden, e.g. in the ear canal (e.g. IIC style).

Having the sound processor for the cochlear implant hidden in the ear canal provides for the benefit, that the sound processor becomes almost invisible. Furthermore, the sound processor is not in the way, when e.g. combing the hair or wearing glasses. Even more, in case the sound processor is placed in the ear canal, the sound processor is more or less protected from direct weather exposure such as rain, snow, sunlight, wind, etc., and external influences, such as high or low temperature, high or low humidity, while it is also less exposed to turbulent wind noise. Furthermore, the natural outer ear sound shaping (directionality) is preserved when having the receiving microphone sitting inside the ear canal opening. In addition, the sound processor is fully accessible by the user and hence, allows service, upgrades and replacements without requiring any surgery or any hardware modification of the implant. Additionally, the cochlear implant does not require a magnet for holding the external antenna, and can thus be made smaller, slimmer and lighter. Further, the cochlear implant can be placed more freely as in the case of a closely matching external antenna, which needs to transmit energy to the cochlear implant, since fewer restrictions are imposed on the cochlear implant.

The inductive antenna 110 of the implantable battery device 100 is placed on top of the antenna of the cochlear implant 310, thus allowing for an efficient coupling between the implantable battery device and the cochlear implant.

Figure 3B:
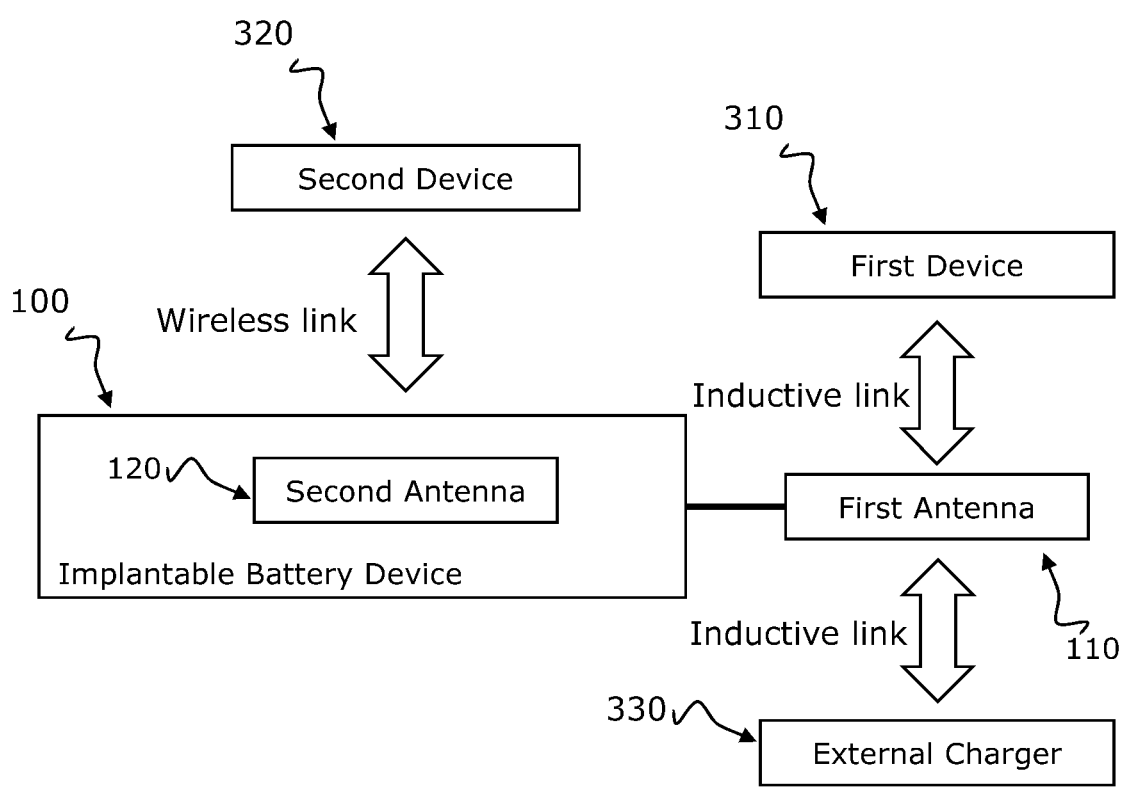
FIG. 3B illustrates a schematic communication diagram according to an embodiment of the disclosure.

Furthermore, in case of battery failure or battery discharge, a standard processor with external inductive antenna as depicted in FIG. 3B can be used as an emergency alternative by the patient to use his cochlear implant, with the implantable battery device 100 in a mode where it is bypassed.

To secure the implantable battery device 100 in place, a magnet in the middle of the inductive antenna can be used, or if the cochlear implant design allows it, the removable magnet of the cochlear implant could be integrated to the inductive antenna 110 of the implantable battery device 100 to secure it on top of the cochlear implant. Any other standard fixation solution (using sutures, dacron mesh or screws for example) could be also used as an alternative or in addition.

In certain embodiments, the implantable battery device 100 may have a rechargeable battery 150. In such a case, it is required to charge the rechargeable battery 150 from time to time.

FIG. 3B shows a situation in which the battery 150 of the implantable battery device 100 is re-charged. An external charger 330 is arranged so that the first antenna 110 of the implantable battery device 100 can receive an electromagnetic field generated by the external charger 330.

Figure 2:
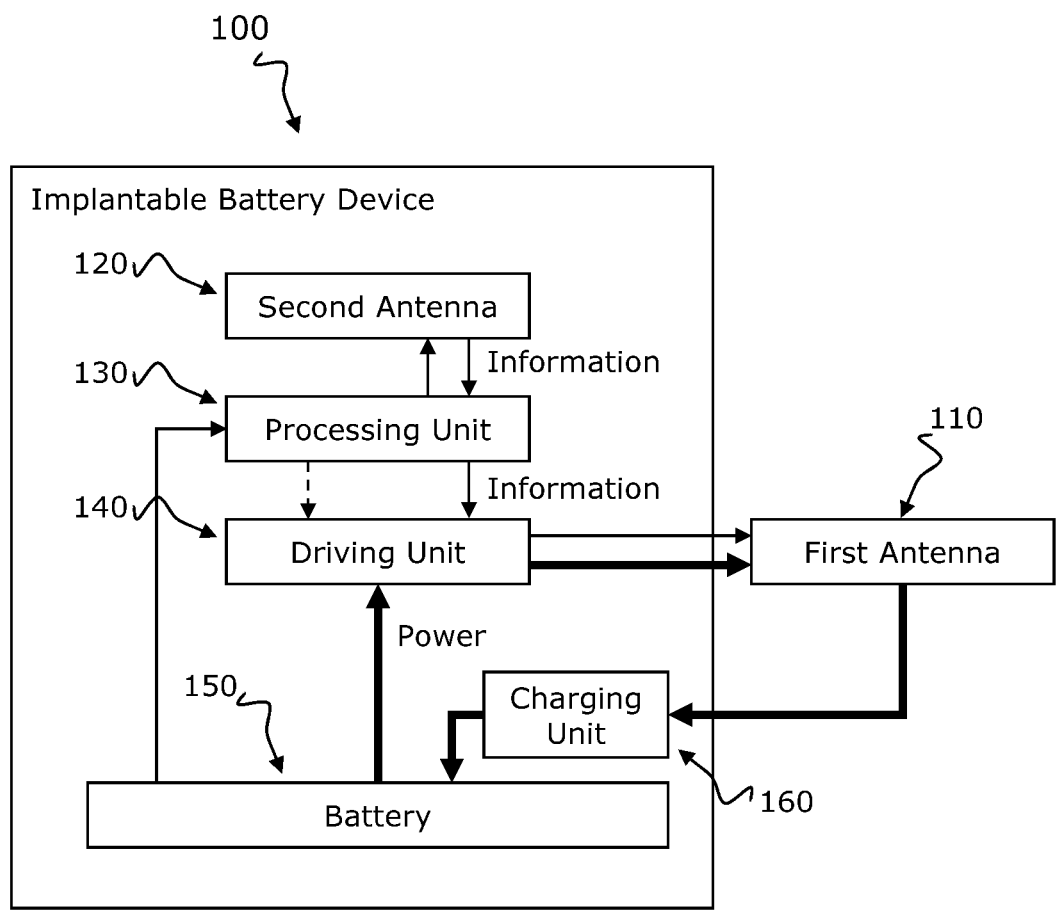
FIG. 2 illustrates a further implantable battery device according to an embodiment of the disclosure.

The implantable battery device 100 as depicted in FIG. 2, additionally comprises a charging unit 160, which is configured to receive energy from the first antenna 110, which picks up energy from an inductive field generated by an external charger device, thus charging the battery 150 of the implantable battery device 100. To control the charging process efficiently, the processing unit 130 may be configured to obtain a charge state of the battery 150. Furthermore, the processing unit may be configured to control the inductive supply of energy to the first device 310 depending on the charge state. Even further, the processing unit 130 may be configured to transmit information to the second device 320 via the second antenna 120 or to the external charger via the second antenna 320 or via the first antenna 110, such as information on the charge state of the battery 150.

In such a situation, it is important that the battery 150 is shielded from the electromagnetic field, which otherwise will induce heat into the battery 150. Such heating will shorten the lifetime of the battery 150.

In certain embodiments of the invention, a temperature sensor is placed on or at the battery 150, thus providing the processing unit with information on the battery temperature. This information can then be transmitted back to the external charger 330 e.g. via the same first antenna 110, which is being used for charging the battery. The temperature can be modulated such that the same coil can be used for both charging and communication at the same time.

A Computer Readable Medium

In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium. For example, the processing in the cochlear implant to adapt the signals for use with the cochlear implant may be rendered in software.

A Data Processing System

In an aspect, a data processing system comprising a processor adapted to execute the computer program for causing the processor to perform at least some (such as a majority or all) of the steps of the method described above and in the claims. For example, the processing in the cochlear implant to adapt the signals for use with the cochlear implant may also be rendered as a data processing system.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

LIST OF REFERENCE SIGNS

100 Implantable Battery Device
110 First Antenna
120 Second Antenna
130 Processing Unit
140 Driving Unit
150 Battery
160 Charging Unit
310 First External Device
320 Second External Device
330 External Charger
400 Stimulation Engine
410 Switched Capacitor Power Supply
420 Voltage Controlled Oscillator
430 Electrode 1
440 Electrode 2
450 Impedance
460 Hold and Sampling
500 Cochlear Implant
510 Battery
520 Magnet Coil
530 Magnet
540 Shield
545 Additional Shielding Element
550 Electrode Array
600 Sound Processor
610 Microphone
620 External Transmitter Antenna
630 External Magnet
640 Internal Magnet, Antenna and Receiver Coil/Stimulator
650 Electrode

The invention claimed is:

1. Implantable battery device, comprising:
a battery,
a first antenna, configured to inductively supply energy from the battery to a first device, and to transmit information received from a processing unit to the first device,
a second antenna for wireless communication with a second device, and
a driving unit, configured to operate the first antenna according to control signals received from the processing unit,
wherein the processing unit is configured to
transmit control signals to the driving unit to control the inductive supply of energy to the first device,
receive information via the second antenna from the second device, said information including audio information obtained via a non-implanted microphone,
transmit the information received via the second antenna from the second device to the first device via the first antenna driven by the driving unit, and
transmit information to the second device via the second antenna, and
wherein the processing unit is configured to control the inductive supply of energy to the first device depending on information received by the second device, said information received by the second device including a user interaction.

2. Implantable battery device according to claim 1,
wherein the driving unit is configured to control an amplitude of an electromagnetic field emitted from the first antenna according to control signals received from the processing unit.

3. Implantable battery device according to claim 2,
wherein the driving unit is configured to modulate the amplitude and/or a frequency of the electromagnetic field emitted from the first antenna according to the information received from the processing unit.

4. Implantable battery device according to claim 2,
wherein the processing unit is configured to transmit information to the second device via the second antenna.

5. Implantable battery device according to claim 2, wherein the processing unit is configured to obtain a charge state of the battery, and to control the inductive supply of energy to the first device depending on the charge state.

6. Implantable battery device according to claim 2, wherein the first antenna comprises a magnetically interacting part in a center of the first antenna for alignment of the first antenna with at least one other antenna.

7. Implantable battery device according to claim 1, wherein the driving unit is configured to modulate the amplitude and/or a frequency of the electromagnetic field emitted from the first antenna according to the information received from the processing unit.

8. Implantable battery device according to claim 7, wherein the processing unit is configured to transmit information to the second device via the second antenna.

9. Implantable battery device according to claim 3, wherein the processing unit is configured to obtain a charge state of the battery, and to control the inductive supply of energy to the first device depending on the charge state.

10. Implantable battery device according to claim 7, wherein the first antenna comprises a magnetically interacting part in a center of the first antenna for alignment of the first antenna with at least one other antenna.

11. Implantable battery device according to claim 1, wherein the processing unit is configured to obtain a charge state of the battery, and to control the inductive supply of energy to the first device depending on the charge state.

12. Implantable battery device according to claim 1, wherein the first antenna comprises a magnetically interacting part in a center of the first antenna for alignment of the first antenna with at least one other antenna.

13. Implantable battery device according to claim 12, wherein the processing unit is configured to obtain a charge state of the battery, and to control the inductive supply of energy to the first device depending on the charge state.

14. Implantable battery device according to claim 1, wherein the battery is a rechargeable battery, and the implantable battery device further comprises a battery charging unit, which is configured to receive energy via the first antenna from another device for recharging the battery.

15. Implantable battery device according to claim 1, wherein the first device is a cochlear implant, and the second device is a hearing aid sound processor of a behind-the-ear (BTE) unit.

16. Implantable battery device according to claim 15, wherein the second device generates the audio information by processing audio signals outputted by the non-implanted microphone, which is attached to the BTE unit, and
wherein the processing unit is configured to process the audio information from the hearing aid sound processor to be transmitted to the cochlear implant.

17. Hearing aid sound processor, configured to transmit audio signals to an implantable battery device according to claim 1 using a wireless link.

18. Charging device, configured to charge an implantable battery device according to claim 1.

* * * * *